United States Patent
Tabata et al.

(10) Patent No.: US 7,349,093 B2
(45) Date of Patent: Mar. 25, 2008

(54) FLUORESCENCE MEASUREMENT APPARATUS

(75) Inventors: Jimpei Tabata, Toon (JP); Satoshi Miyagawa, Niihama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 91 days.

(21) Appl. No.: 11/346,235

(22) Filed: Feb. 3, 2006

(65) Prior Publication Data

US 2007/0002325 A1    Jan. 4, 2007

(30) Foreign Application Priority Data

Feb. 17, 2005    (JP)    ............... 2005-040163

(51) Int. Cl.
 *G01J 3/30*    (2006.01)
(52) U.S. Cl. ..................... 356/417; 356/244
(58) Field of Classification Search ............... 356/417, 356/246
See application file for complete search history.

(56) References Cited

U.S. PATENT DOCUMENTS

| | | | |
|---|---|---|---|
| 4,431,307 A * | 2/1984 | Suovaniemi | ............... 356/246 |
| 5,238,815 A | 8/1993 | Higo et al. | |
| 2001/0028458 A1* | 10/2001 | Xiao | ............... 356/417 |
| 2004/0182710 A1 | 9/2004 | Tanaami | |
| 2004/0184960 A1 | 9/2004 | Tanaami | |
| 2004/0234417 A1* | 11/2004 | Schienle et al. | ......... 422/82.08 |
| 2005/0051744 A1* | 3/2005 | Emoto | ............... 250/576 |
| 2005/0176003 A1 | 8/2005 | Yokoyama et al. | |
| 2005/0206895 A1* | 9/2005 | Salmelainen | ............... 356/318 |
| 2006/0262309 A1* | 11/2006 | Banks | ............... 356/417 |

FOREIGN PATENT DOCUMENTS

| | | |
|---|---|---|
| JP | 6-60901 | 3/1987 |
| JP | 6-95073 | 11/1994 |
| JP | 2624655 | 4/1997 |
| JP | 2000-338035 | 12/2000 |
| JP | 2002-286627 | 10/2002 |
| JP | 2003-130873 | 5/2003 |
| JP | 2003-183425 | 7/2003 |
| JP | 2004-279306 | 10/2004 |

* cited by examiner

*Primary Examiner*—Kara Geisel
(74) *Attorney, Agent, or Firm*—Wenderoth, Lind & Ponack, L.L.P.

(57) ABSTRACT

On a substrate 41 holding a sample to be detected, a dielectric multilayer 42 is disposed which reflects excitation light e1 supplied from above the substrate 41 and transmits fluorescence f1 emitted from the sample, and the excitation light e1 is reflected at the dielectric multilayer 42 while the transmitted fluorescence f1 is detected by a light receiving unit 44, thereby providing a fluorescence measurement apparatus which can resolve a problem of reduction in detection sensitivity due to autofluorescence from the substrate or leakage of the excitation light from a light receiving filter, and which can detect the sample with high sensitivity.

16 Claims, 5 Drawing Sheets

FLUORESCENCE MEASUREMENT APPARATUS

FIELD OF THE INVENTION

The present invention relates to a fluorescence measurement apparatus for measuring fluorescence emitted from a sample that is irradiated with excitation light, and more particularly, to a fluorescence measurement apparatus which reduces autofluorescence of a substrate that holds the sample.

BACKGROUND OF THE INVENTION

Conventionally, as a method for detecting biomolecules such as nucleic acid, protein, and enzyme, a fluorescence measurement method utilizing fluorescence reaction has been adopted. Since the fluorescence measurement method can perform measurement of biomolecules safely and inexpensively by combining existing optical components such as a light source and a light receiving unit without using a radioisotope, it is applied to various kinds of biomolecule detection methods such as enzyme immunoassay, electrophoresis, and confocal scanning fluorescence microscopy.

The fluorescence measurement is a method for detecting a fluorescence signal emitted from a sample by irradiating the sample with excitation light. For example, FITC (fluorescein isothiocyanate) is a substance that emits fluorescence having a wavelength of 520 nm when it is irradiated with excitation light having a wavelength of 495 nm. In order to detect a substance that emits fluorescence, the fluorescence is measured by a combination of light having an excitation wavelength and a light receiving unit for detecting a fluorescence wavelength. As a practical application thereof, a fluorescence measurement method is proposed in which excitation light irradiates a sample, and the fluorescence depending on the excitation light is detected by a light receiving unit disposed on the irradiation side of the excitation light (for example, refer to Japanese Published Examined Patent Application No. Hei. 6-60901 (Patent Document 1)). FIG. 10 shows a schematic diagram of a conventional fluorescence measurement apparatus. With reference to FIG. 10, excitation light e1, which is emitted from an excitation light source 103 and reflected by a dichroic mirror 107, irradiates a sample 106 disposed on a substrate 101. Fluorescence f1 emitted from the sample 106 that is excited by the excitation light e1 is transmitted through the dichroic mirror 107 and a bandpass filter 108 to be detected by the light receiving unit 104 as a fluorescence signal. In this way, various kinds of fluorescent samples and fluorescently-labeled biomolecules can be detected by using a substance that emits fluorescence, and excitation light and a light receiving unit corresponding to the fluorescence.

When performing a fluorescence measurement, a substrate, a cell, a channel or the like for holding a sample is used (hereinafter referred to simply as "substrate"). As a material of the substrate, silica glass having a high transparency to ultraviolet light has conventionally been adopted. However, recently, high-polymer materials that are easily moldable and disposable have been used. Although, as described above, such high-polymer materials are easily moldable, they tend to emit autofluorescence when irradiated with excitation light. Since autofluorescence from the substrate 101 has a similar wavelength region to that of the fluorescence f1, the autofluorescence transmits through the dichroic mirror 107 and the bandpass filter 108 to reach the light receiving unit 104. The autofluorescence causes background noise, thereby worsening the S/N ratio of the measurement. Accordingly, various methods for reducing autofluorescence from the substrate 101 have conventionally been proposed (refer to Japanese Published Patent Application No. 2000-338035 (Patent Document 2), Japanese Published Patent Application No. 2002-286627 (Patent Document 3), Japanese Published Examined Patent Application No. Hei. 6-95073 (Patent Document 4), Japanese Published Patent Application No. 2003-130873 (Patent Document 5), and Japanese Published Patent Application No. 2003-183425 (Patent Document 6)).

For example, Patent Document 2 proposes a method of performing spectrofluorometric measurement. A fluorescence wavelength from a sample is slightly different from an autofluorescence wavelength from a substrate, whereby fluorescence can be separated from autofluorescence. Patent Document 3 proposes a method of reducing autofluorescence from a substrate by covering a part of the substrate other than a fluorescence measurement part with a light shielding film. Further, Patent Document 4 proposes a method for preventing emission of autofluorescence from a substrate by reflecting excitation light with a reflection layer such as a metal layer or a dielectric multilayer that is disposed on the surface of the substrate where a fluorescent substance is disposed. Furthermore, Patent Document 5 and Patent Document 6 propose a method of making a material of a substrate so as not to emit autofluorescence.

Furthermore, also when using fluorescence measurement for measuring a sample that performs electrophoresis, the above-mentioned fluorescence measurement method is adopted (for example, refer to Japanese Patent No. 2624655 (Patent Document 7)). Also in this case, as described above, autofluorescence emitted from a substrate as a channel causes background noise during fluorescence measurement, thereby worsening detection sensitivity.

In order to solve this problem, Japanese Published Patent Application No. 2004-279306 (Patent Document 8) proposes a method in which a region other than a measurement part is covered with a light shielding part, and excitation light irradiates a side surface of an electrophoresis gel cassette as a substrate, thereby preventing the electrophoresis gel cassette from emitting autofluorescence.

As described above, a technique for detecting a small signal of sample with high sensitivity has recently been demanded. Therefore, various methods have been developed for reducing influences of autofluorescence emitted from a substrate, leakage of excitation light, and background noise such as scattered light, in a technique of irradiating a sample with excitation light and analyzing light emitted from the sample.

However, the above-mentioned respective methods for reducing influence of autofluorescence from a substrate have the following drawbacks.

In the method of separating autofluorescence from a fluorescence signal by spectrofluorometric measurement, which is proposed by Patent Document 2, since the wavelength region of the autofluorescence and the wavelength region of the fluorescence from the sample are approximately equal to each other or broadly overlap each other, it is difficult to completely separate them by spectrofluorometric measurement. Therefore, the autofluorescence signal is undesirably added over the fluorescence signal. Especially when measuring a sample having a small fluorescence signal, a fluorescence signal is difficult to detect because of an autofluorescence signal, which makes it difficult to detect a small fluorescence of sample with high sensitivity.

Further, in the method of reducing autofluorescence from a substrate by covering a part of a substrate other than a fluorescence measurement part, which is proposed by Patent Document 3, autofluorescence undesirable occurs from a bottom of a sample holder. Therefore, when measuring a sample emitting a small fluorescence signal, a fluorescence signal is difficult to detect because of an autofluorescence signal, which makes it difficult to perform highly sensitive detection. Moreover, thin film fabrication processes for the light shielding film are complicated.

Further, in the method of preventing autofluorescence from a substrate by reflecting excitation light using a reflection layer comprising a metal or a dielectric multilayer, which is disposed on the surface of the substrate on which a fluorescent substance is disposed, which method is proposed by Patent Document 4, since a dichroic mirror and a light receiving filter have a transmittance limit of $10~10^{-6}\%$ ((leakage light intensity/incident light intensity)×100(%)), it is difficult to completely cut the reflected excitation light, and the leakage light of the excitation light from the filter causes a noise signal. Especially when measuring a sample having a small fluorescence signal, the noise signal significantly deteriorates the S/N ratio.

Further, in the method for making a material itself of a substrate so as not to emit autofluorescence, which is proposed by Patent Documents 5 and 6, it is difficult to completely prevent the material from emitting autofluorescence, and therefore, a small amount of autofluorescence is emitted from the substrate. Especially when measuring a sample having a small fluorescence signal, the autofluorescence significantly deteriorates the S/N ratio.

Further, in the method of irradiating excitation light onto a side surface of an electrophoresis gel cassette by fluorescence measurement in electrophoresis, when irradiating the excitation light onto the side surface of the electrophoresis gel cassette, it is difficult to irradiate the excitation light to the entire gel evenly, and moreover, a complicated optical control for irradiating the excitation light onto the side surface of the electrophoresis gel cassette is required. Therefore, this method is not practical.

As described above, there have conventionally been proposed various methods for reducing the influence of autofluorescence. However, none of these methods has sufficient performance for detecting a small amount of sample signal.

SUMMARY OF THE INVENTION

The present invention is made to solve the above-described problems and has for its object to provide a fluorescence measurement apparatus which can detect a measurement sample with high sensitivity.

In order to solve the above-mentioned problems, in a fluorescence measurement apparatus according to the present invention, a wavelength selection means is formed on an upper surface of a substrate which holds a sample that emits fluorescence when being irradiated with excitation light, which wavelength selection means reflects the excitation light and transmits the fluorescence; the sample is disposed on the substrate on which the wavelength selection means is formed; the excitation light irradiates the sample from above the substrate; and the fluorescence emitted from the sample, which has passed through the wavelength selection means, is detected by a light receiving unit that is disposed beneath the substrate.

Therefore, influence of autofluorescence emitted from the substrate due to the excitation light can be significantly reduced, resulting in highly sensitive measurement.

Further, the wavelength selection means comprises a coating layer that is formed on the upper surface of the substrate.

Further, the coating layer comprises a dielectric multilayer.

Further, the dielectric multilayer is obtained by alternately depositing at least one kind of dielectric material having a high refractive index, and at least one kind of dielectric material having a refractive index lower than that of the high refractive index dielectric material.

Further, the wavelength selection means comprises titanium dioxide layers and silicon dioxide layers which are alternately deposited.

Therefore, the wavelength selection means can reflect the excitation light irradiated to the sample, and transmit the fluorescence emitted from the sample.

Further, between the substrate and the light receiving unit, a filter is provided for transmitting only the fluorescence that has been emitted from the sample and passed through the wavelength selection means.

Therefore, fluorescence detecting can be carried out with higher sensitivity.

Further, the substrate comprises a high-polymer material.

Therefore, it is possible to obtain a substrate which can easily be shaped and is disposable.

Further, the substrate is a flat plate in shape, the wavelength selection means is formed on the entire upper surface of the substrate, and the sample is disposed on the wavelength selection means.

Therefore, the fluorescence from the sample disposed on the flat-plate-shaped substrate can be detected with higher sensitivity.

Further, the substrate has a well or a channel formed in its upper portion, the wavelength selection means is formed at a bottom surface of the well or the channel that is formed in the substrate, and the sample is disposed in the well or the channel in which the wavelength selection means is formed.

Therefore, the fluorescence from the sample disposed in the well or the channel of the substrate can be detected with higher sensitivity.

Further, the substrate has a well or a channel formed in its upper portion, the wavelength selection means is formed at a bottom surface and inner side surfaces of the well or the channel that is formed in the substrate, and the sample is disposed in the well or the channel in which the wavelength selection means is formed.

Therefore, when the excitation light diagonally irradiates the sample disposed in the well or the channel of the substrate, the excitation light is reflected by the wavelength selection means which is formed on the side surfaces or the bottom surface of the well or the channel so that the reflected excitation light again irradiates the sample, whereby the fluorescence signal from the sample can be increased.

Further, a top plate having, on its one surface, a reflection layer for reflecting the excitation light is deposited with the reflection layer facing the substrate, and the excitation light is multiple-reflected in the sample by the wavelength selection means and the reflection layer that is formed on the one surface of the top plate.

Therefore, the excitation light is reflected multiple times between the wavelength selection means and the reflection layer of the top plate, whereby the reflected excitation light can irradiate the sample multiple times. Consequently, the fluorescence from the sample can be amplified, whereby fluorescence detection can be carried out with high sensitivity.

EFFECTS OF THE INVENTION

According to a fluorescence measurement apparatus of the present invention, a wavelength selection means is provided on an upper surface of a substrate holding a sample that emits fluorescence when being irradiated with excitation light, which wavelength selection means reflects the excitation light and transmits the fluorescence, and the fluorescence that has passed through the wavelength selection means is measured by a light receiving unit. Therefore, autofluorescence from the substrate due to the excitation light is not emitted, resulting in highly sensitive measurement of a small amount of fluorescent sample. Further, since the wavelength selection means reflects the excitation light and the reflected excitation light again irradiates the sample, the fluorescence can be increased.

Furthermore, according to the fluorescence measurement apparatus of the present invention, a top plate having, on its one surface, a reflection layer for reflecting the excitation light is disposed on a substrate, and a sample is held with the wavelength selection means and the reflection layer of the top plate. Therefore, fluorescence can be amplified by irradiating the sample with the excitation light multiple times, whereby a small amount of fluorescent substance can be measured with higher sensitivity.

DETAILED DESCRIPTION OF THE PREFERRED EMBODIMENTS

Embodiment 1

Hereinafter, a fluorescence measurement apparatus according to a first embodiment of the present invention will be described with reference to the drawings.

Initially, the construction of a substrate according to the first embodiment will be described with reference to FIGS. 1~3. In this first embodiment, a "substrate" means any of a substrate, a cell, and a channel on which a sample is disposed.

Figure 1:
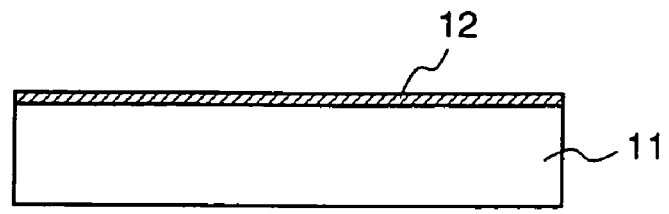
FIG. 1 is an end view illustrating a structure of a substrate having a dielectric multilayer on its plane surface, according to a first embodiment of the present invention.
Figure 2:
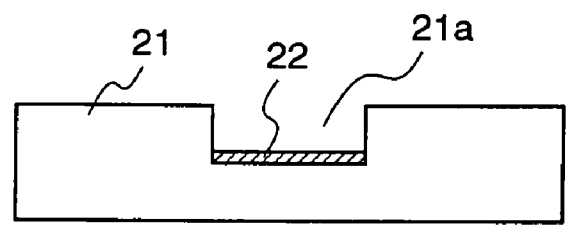
FIG. 2 is an end view illustrating a structure of a substrate having a well or a channel in which a dielectric multilayer is deposited, according to the first embodiment of the present invention.
Figure 3:
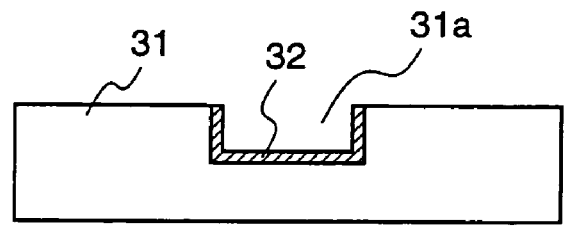
FIG. 3 is an end view illustrating another structure of a substrate having a well or a channel in which a dielectric multilayer is disposed, according to the first embodiment of the present invention.

FIGS. 1~3 are end views illustrating examples of substrates according to the first embodiment. FIG. 1 shows a flat-plate-shaped substrate, and FIGS. 2 and 3 show substrates on which concave wells or channels are formed, respectively.

As shown in the figures, the substrates 11, 21, and 31 according to the first embodiment are provided with wavelength selection means 12, 22, and 32, respectively, for reflecting excitation light, and transmitting fluorescence that is emitted from samples disposed on the respective substrates. The wavelength selection means 12, 22, and 32 are obtained by forming layers on the substrates, and each layer may be fabricated as such as a dielectric multilayer.

For example, when the substrate 11 is flat like a microarray (DNA chip) as shown in FIG. 1, a dielectric multilayer 12 is formed over the entire surface of the substrate 11 as the wavelength selection means.

On the other hand, when a concave well or channel 21a is formed at the surface of the substrate 21, like a micro plate (well plate) or a micro channel chip, a dielectric multilayer 22 is formed as the wavelength selection means at the bottom of the concave well or channel 21a. A sample to be measured is disposed on the dielectric multilayer 22. The concave well or channel 21a may have a V or U-shaped cross-section or a circular cross-section.

As described above, the wavelength selection means 12 or 22 for reflecting the excitation light and transmitting the fluorescence emitted from the sample are disposed on the upper surface of the substrate 11 or 21 that holds the sample, respectively. Therefore, it is possible to significantly reduce influence of autofluorescence emitted from the substrate 11 or 21, which occurs when the substrate 11 or 21 is irradiated with the excitation light.

Further, as shown in FIG. 3, the dielectric multilayer 32 may be disposed not only on the bottom of the concave well or channel 31a formed at the surface of the substrate 31 but also on the internal side surfaces of the well or channel 31a. Thereby, even when the excitation light supplied from above the substrate 31 is not vertically incident on the surface of the substrate 31, the excitation light can be reflected at the dielectric multilayer 32 deposited on the internal side surfaces of the well or channel 31a, whereby the influence of the autofluorescence from the substrate 31 can be further reduced.

Next, the dielectric multilayer formed on the substrate will be described in detail.

The dielectric multilayer 12, 22, or 32 is obtained by combining at least one kind of dielectric material having a high refractive index and at least one kind of dielectric material having a low refractive index that is lower than that of the high-refractive-index dielectric material.

To be specific, the dielectric multilayer 12, 22, or 32 is formed by alternately depositing the high refractive index film and the low refractive index film, or by simultaneously vapor-depositing the high refractive index dielectric material and the low refractive index dielectric material so as to mix them. Considering the easiness of fabrication and the easiness of controlling optical transparency, the dielectric multilayer is desired to have a structure in which the high refractive index film and the low refractive index film are alternately deposited.

The high refractive index film is selected from a group consisting of tantalum pentoxide, niobium pentoxide, titanium pentoxide, titanium dioxide, and zirconium dioxide, and the low refractive index film is selected from a group consisting of silicon dioxide and a fluorinated material.

The dielectric multilayer 12, 22, or 32 on the substrate 11, 21, or 31 can be obtained by a conventional thin-film fabrication process, such as vacuum deposition, thermal deposition, electron beam deposition, sputtering, ion plating, or CVD (Chemical Vapor Deposition). Further, a desired layer thickness of a high repeatability of refractive index can be obtained by controlling the deposition rate of the dielectric multilayer.

In the case where a mixture layer is to be formed as the dielectric multilayer, for example, niobium pentoxide having a high refractive index (2.3) and silicon dioxide having a low refractive index (1.5) are simultaneously vapor-deposited on the substrate so as to mix them, whereby a mixture layer having a refractive index of 1.9 can be obtained.

On the other hand, in the case where a layer in which plural dielectric materials are alternately deposited is to be formed as the dielectric multilayer, for example, a high refractive index film comprising niobium pentoxide and a low refractive index film comprising silicon dioxide are alternately deposited by reactive sputtering on the substrate.

The transmission characteristic of the wavelength of the dielectric multilayer 12, 22, or 32 fabricated as described above is determined according to a fluorescence material, and it is selected so as to shield the excitation light and transmit the fluorescence that occurs from the sample due to the excitation light. This selection of the transmission characteristic of the dielectric multilayer is carried out by selecting materials of the dielectric multilayer, and controlling the composition of the layers, or the thickness of each layer, or the number of layers.

More specifically, in the case where a mixture layer is to be formed as the dielectric multilayer, dielectric materials are selected, and the composition ratio is controlled by the deposition rate of each dielectric material, whereby desired a transmission characteristic can be obtained. On the other hand, in the case where a layer in which plural kinds of dielectric materials are deposited is to be formed as the dielectric multilayer, the thickness of each layer and the number of layers should be varied, in addition to selection of the dielectric materials to be deposited, whereby a desired transmission characteristic can be obtained.

In order to obtain a desired transmission characteristic of the dielectric multilayer, a conventional method such as spectral simulation or spectral sensitivity characteristic measurement can be adopted.

For example, it is possible to determine a wavelength region in which no light transmits (cutoff region). When the cutoff region ranges from 400 nm to 500 nm, it is possible to detect FITC (fluorescence excitation wavelength: 495 nm, fluorescence wavelength: 520 nm) and Alexa Fluor 430 (fabricated by Molecular Probes, fluorescence excitation wavelength: 430 nm, fluorescence wavelength: 540 nm), using the same dielectric multilayer.

As wavelength filters having the same characteristic as that of the wavelength selection means of the present invention, a band-pass filter, a short wavelength cutoff filter, a dichroic filter, and a cold filter have actually been marketed.

The substrates 11, 21, and 31 comprise a glass or a high-polymer material. The high-polymer material is any of polymethylmethacrylate, polyacrylonitrile, polyethylene terephthalate, polyimide, polycarbonate, polystyrene, polyethylene, polypropylene, Teflon (trademark), polyethylene fluoride, melamine, and nylon, or a mixture thereof.

Figure 4:
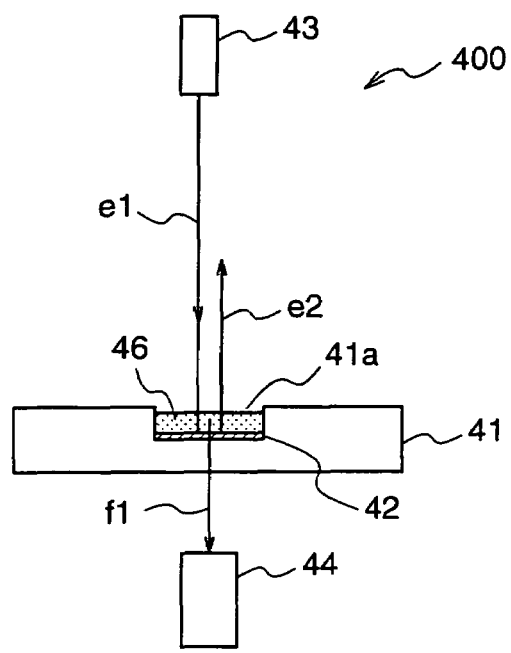
FIG. 4 is a schematic diagram illustrating a construction of a fluorescence measurement apparatus according to the first embodiment of the present invention.

Next, an example a fluorescence measurement apparatus according to the present invention will be described with reference to the drawings. FIG. 4 is a schematic diagram illustrating a construction of the fluorescence measurement apparatus according to the first embodiment. In FIG. 4, a sample to be measured is disposed in, for example, a micro channel which is formed on a substrate.

In the fluorescence measurement apparatus 400 according to the first embodiment, an excitation light source 43 for emitting excitation light e1 having a fluorescence excitation wavelength is disposed above a substrate 41, and a light receiving unit 44 for measuring fluorescence emitted from a sample irradiated with the excitation light e1 is disposed beneath the substrate 41, i.e., on the opposite side of the excitation light source 43. The excitation light e1 emitted from the excitation light source 43 irradiates the sample 46 that is disposed on the dielectric multilayer 42 formed at the bottom of the channel 41a of the substrate 41, and fluorescence f1 is emitted from the sample 46 irradiated with the excitation light e1. The fluorescence f1 emitted from the sample 46 transmits through the dielectric multilayer 42 to be measured by the light receiving unit 44. The excitation light component which has not been used for fluorescence excitation is reflected by the dielectric multilayer 42 as reflected light e2 upward from the substrate 41.

As described above, in the fluorescence measurement apparatus 400 according to the first embodiment, since the excitation light that has not been used for fluorescence excitation is reflected by the dielectric multilayer 42, no autofluorescence occurs from the substrate 41 due to the excitation light. Accordingly, the problem of reduction in detection sensitivity due to autofluorescence from the substrate 41 is resolved, whereby the target sample can be detected with high sensitivity. Further, since the reflected light e2 at the dielectric multilayer 42 again irradiates the sample 46, the fluorescence f1 from the sample 46 can be increased.

When the fluorescence measurement apparatus 400 is constituted so that the excitation light emitted from the excitation light source 43 is focused on the sample 46, a very small amount of sample signal can be detected.

Figure 5:
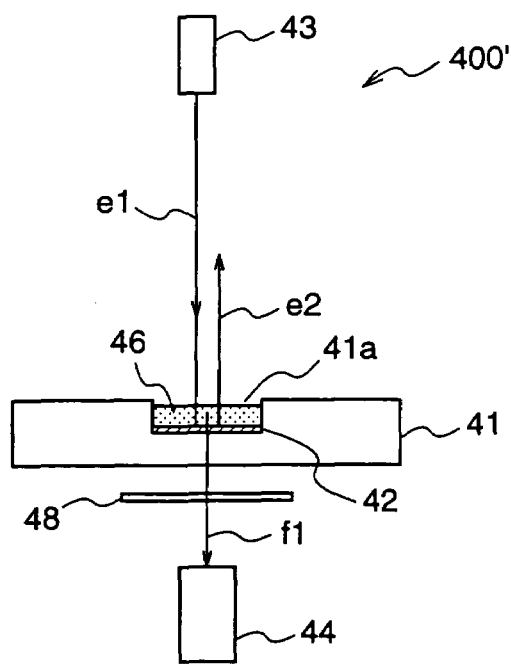
FIG. 5 is a schematic diagram illustrating another construction of a fluorescence measurement apparatus according to the first embodiment of the present invention.

Further, when the secondary autofluorescence is emitted from the substrate 41 due to the fluorescence emitted from the sample 46, the wavelength of the secondary autofluorescence is shifted toward the longer wavelength region than the wavelength of the fluorescence f1 emitted from the sample. Thereby, influence of the noise can also be resolved by disposing a light-receiving filter 48 for shutting out wavelengths other than the wavelength of the fluorescence f1 on the optical path that guides the fluorescence f1 to the light receiving unit 44, as shown by a fluorescence measurement apparatus 400' in FIG. 5. Further, noise such as leakage light or scattering light of the excitation light, the excitation wavelength can also be shut off by disposing a light receiving filter (not shown) for shutting off the excitation wavelength, on the optical path that guides the fluorescence f1 to the light receiving unit 44.

Figure 6:
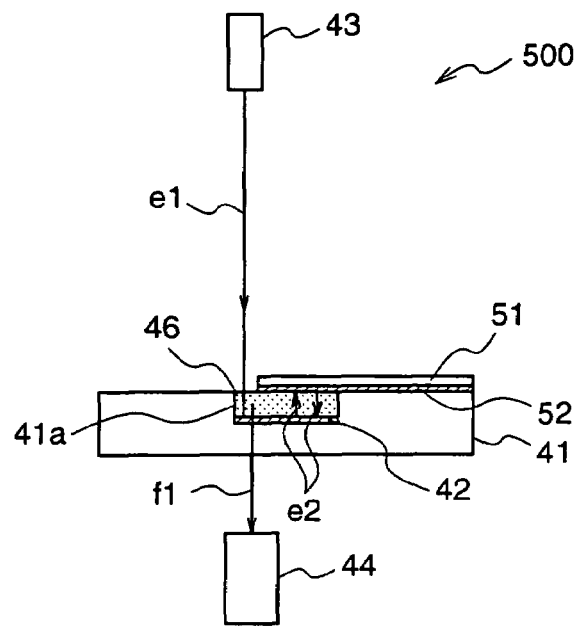
FIG. 6 is a schematic diagram illustrating still another construction of a fluorescence measurement apparatus according to the first embodiment of the present invention.

Further, in the case where a concave well or channel 41a such as a micro channel is formed on the substrate 41, as shown in a fluorescence measurement apparatus 500 in FIG. 6, a top plate 51 having, on one surface thereof, reflection layer 52 for reflecting the excitation light e2 reflected at the dielectric multilayer 42 may be disposed on the upper side of the well or channel 41a of the substrate 41 so that the reflection layer 52 faces the substrate 41, whereby the reflected light e2 that is the excitation light component reflected at the dielectric multilayer 42 is reflected multiple times between the reflection layer 52 of the top plate 51 and the dielectric multilayer 42, that is, the reflected light e2 is multiple-reflected in the sample 46. Thereby, the fluorescence f1 emitted from the sample 46 is further increased, and the fluorescent substance can be detected with higher sensitivity by the light receiving unit 44.

As the reflection layer 52 formed on the top plate 51, a layer comprising a mirror material such as aluminum or silver, or a coating layer such as the dielectric multilayer 42 formed on the substrate 51 may be adopted. However, the thin film comprising a mirror material that totally reflects the reflected light e2 is more preferable. Further, as shown in FIG. 6, the top plate 51 is disposed so as not to cover the entire opening of the concave well 41a formed in the substrate 41, that is, the top plate 51 is disposed so as to open a region where the excitation light e1 emitted from the excitation light source 43 can directly irradiate the sample 46.

Example 1

Figure 7:
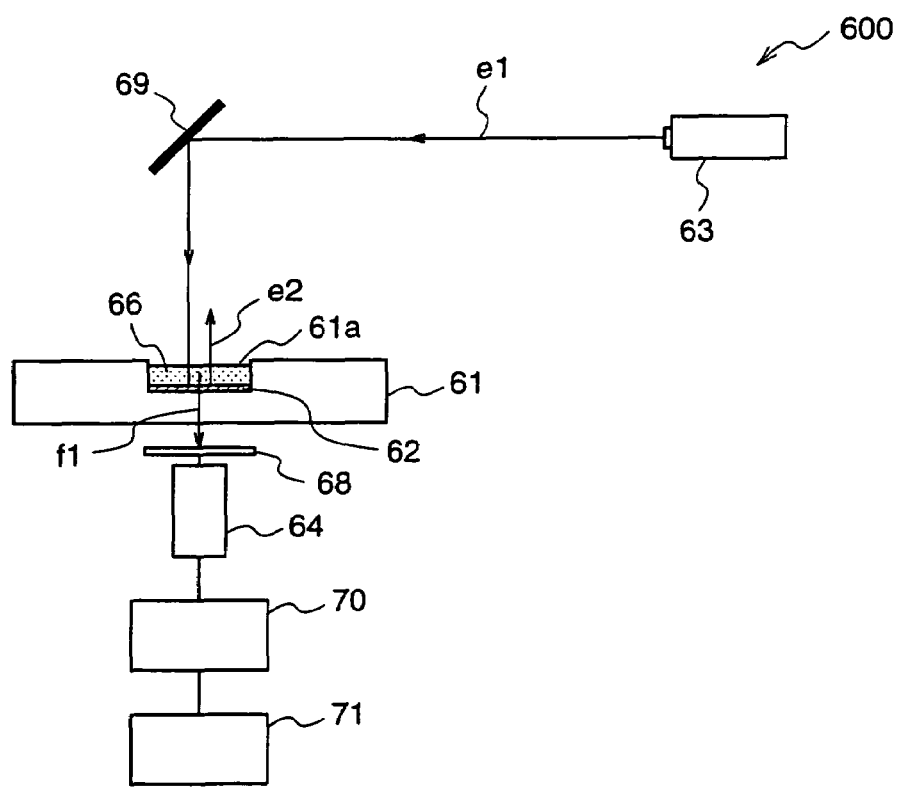
FIG. 7 is a schematic diagram illustrating a construction of a fluorescence measurement apparatus according to a first example of the present invention.

Hereinafter, an example of a fluorescence measurement apparatus will be described with reference to FIG. 7. The fluorescence measurement apparatus of the present invention is not restricted to the construction described hereinafter.

(1) Fabrication of Substrate

A substrate 61 comprising a high-transparency polymethylmethacrylate, in which a concave channel 61a having a width of 80~120 μm and a depth of 30~70 μm is formed at the surface, is prepared, and a dielectric multilayer 62 is coated at the bottom surface of the channel 61a.

The dielectric multilayer 62 has a construction in which a high refractive index layer A (titanium dioxide, refractive index 2.4) and a low refractive index layer B (silicon dioxide, refractive index 1.5) are alternately deposited. Both the high refractive index layer A and the low refractive index layer B are deposited by reactive sputtering.

Hereinafter, film depositing conditions by reactive sputtering used in this example will be described. The conditions for depositing the high refractive index layer A are as follows: power of 4500 W, 250 sccm of argon gas, and 120 sccm of oxygen gas are adopted here, and titanium is used as a target. The thickness of the high refractive index layer A under the sputtering conditions is 20~50 nm. The conditions for depositing the low refractive index layer B are as follows: power of 9000 W, 250 sccm of argon gas, and 120 sccm of oxygen gas are adopted here, and silicon is used as a target. The thickness of the low refractive index layer B under the sputtering conditions is 60~90 nm.

Figure 8:
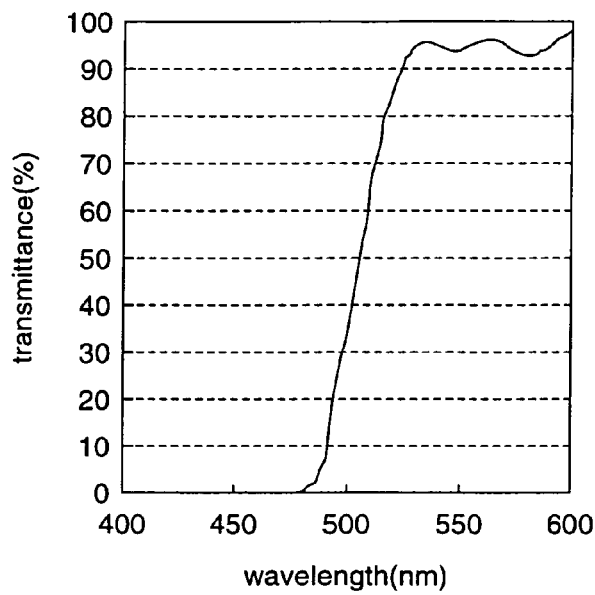
FIG. 8 is a diagram illustrating optical transmission characteristics of a substrate having a well in which a dielectric multilayer is deposited, which is fabricated in the first example of the present invention.

In this first embodiment, the high refractive index layer A and the low refractive index layer B are alternately deposited thirty times to form the dielectric multilayer 62 having a total thickness of about 1.2 μm~2.1 μm. Preferably, a dielectric multilayer of 1.7 μm should be deposited. FIG. 8 is a diagram illustrating light transmission characteristics of the substrate having the dielectric multilayer fabricated in this first example.

(2) Fluorescence Measurement by Fluorescence Measurement Apparatus

Next, a description will be given of a fluorescence measurement apparatus 600 using the substrate 61 fabricated as described above.

An excitation light source 63 emits the excitation light e1 (center wavelength: 470 nm). The excitation light e1 reflected by a mirror 69 irradiates a FITC-labeled sample 66 which is disposed in the channel of the substrate 61.

Fluorescence f1 emitted from the sample 66 due to the excitation light e1 transmits through the substrate 61 and a light receiving filter 68, and the amount of the fluorescence f1 is counted and detected by a light receiving unit 64 (photo counter) disposed on the opposite side of the substrate 61 from the irradiation side of the excitation light. Further, an excitation light component (reflected light) e2 which has not been used for the fluorescence excitation is reflected by the dielectric multilayer 62. Then, fluorescence signal data detected by the light receiving unit 64 is stored in an external memory 70, and further, is outputted by an output mechanism 71.

As a result of detection by the fluorescence measurement apparatus 600 constituted as described above, a fluorescence signal of 3 fmol minimum is obtained.

Example 2

Figure 9:
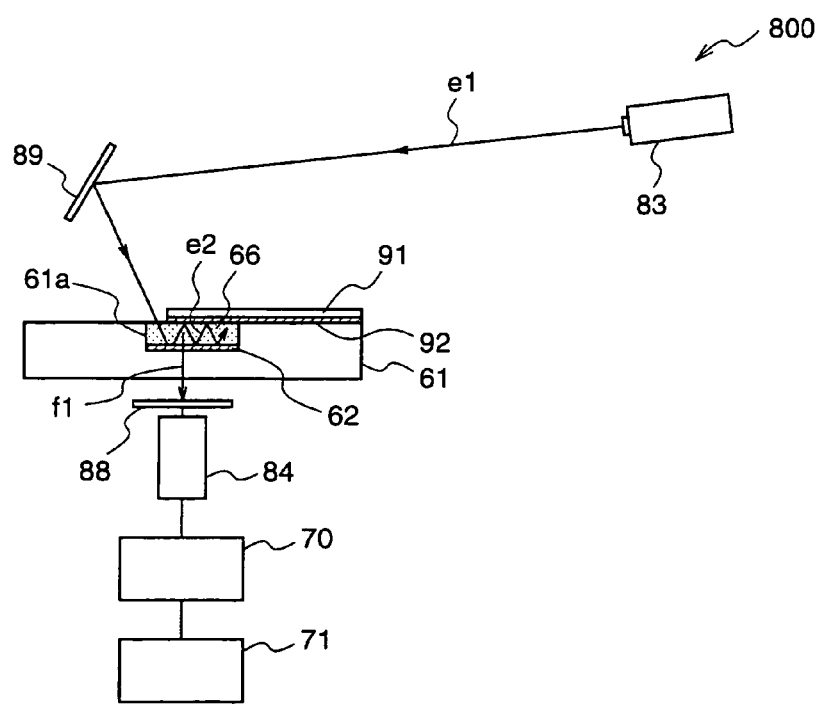
FIG. 9 is a schematic diagram illustrating a construction of a fluorescence measurement apparatus according to a second example of the present invention.
Figure 10:
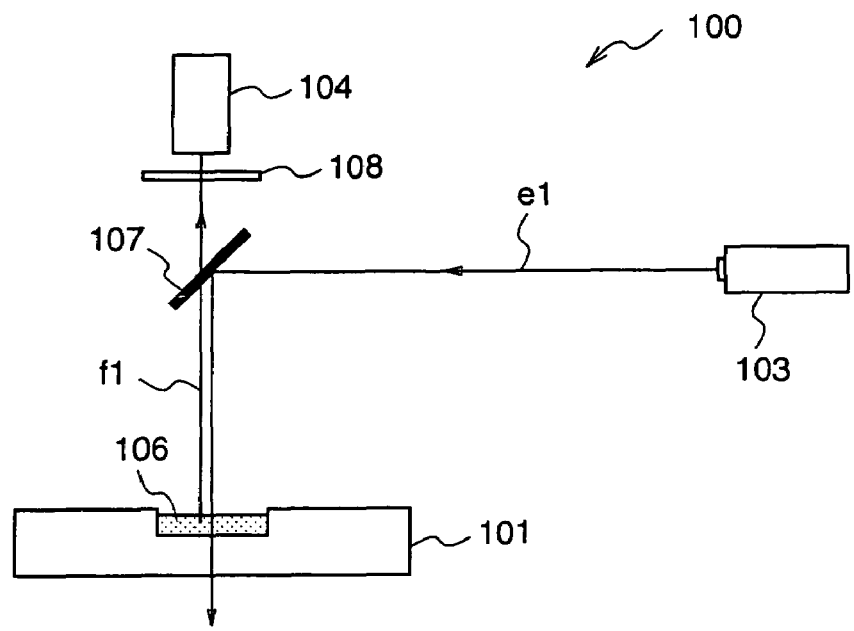
FIG. 10 is a schematic diagram illustrating a construction of a conventional fluorescence measurement apparatus.

Hereinafter, another example of a fluorescence measurement apparatus will be described with reference to FIG. 9. The fluorescence measurement apparatus of the present invention is not restricted to the construction described hereinafter.

(1) Fabrication of Substrate

A substrate 61 on which a dielectric multilayer 62 is deposited, which is used in this second example, is fabricated in the same method as that described for the first example.

(2) Placement of Top Plate

In this second example, a top plate 91 having, on its one surface, deposition of a reflection layer 92 that reflects the excitation light emitted from the excitation light source 63, is disposed on the concave channel 61a formed in the substrate 61 so that the reflection layer 92 faces the substrate 61. At this time, the top plate 91 is disposed on the substrate 61 so as not to entirely cover the opening of the channel 61a that is formed in the substrate 61, i.e., the top plate 91 is disposed so as to secure a space through which the excitation light directly irradiates the sample 66.

(3) Fluorescence Measurement by Fluorescence Measurement Apparatus

Next, a description will be given of a fluorescence measurement apparatus 800 using the substrate 61 on which the top plate 91 is disposed so as to cover a part of the channel 61a formed in the substrate 61.

An excitation light source 83 emits excitation light e1 (center wavelength: 470 nm). The excitation light e1 reflected by a mirror 89 irradiates a FITC-labeled sample 66 which is disposed in the channel of the substrate 61. The excitation light e1 from the excitation light source 83 directly irradiates the sample 66 without irradiating the top plate 91.

Fluorescence f1 emitted from the sample 66 due to the excitation light e1 transmits through the substrate 61 and a light receiving filter 88, and the amount of the fluorescence f1 is counted and detected by a light receiving unit 84 (photo counter) disposed on the opposite side of the substrate 61 from the irradiation side of the excitation light. Further, an excitation light component (reflected light) e2 which has not been used for the fluorescence excitation is reflected by the dielectric multilayer 62 formed on the substrate 81, and further, is totally reflected by a reflection thin film 92 formed on the top plate 91. This reflection causes multiple reflection in the channel, whereby the fluorescence f1 is amplified. Then, the fluorescence signal data detected by the light receiving unit 84 is stored in an external memory 70 and outputted by an output mechanism 71.

As a result of detection by the fluorescence measurement apparatus 800 constituted as described above, a fluorescence signal of 2 fmol is obtained from the smallest sample.

As described above, according to the fluorescence measurement apparatus of the first embodiment, the wavelength selection means comprising a dielectric multilayer that reflects excitation light emitted from above the substrate and transmits fluorescence emitted from the sample is disposed on the substrate on which the sample is disposed, and the fluorescence that has passed through the wavelength selection means is detected by the light receiving unit. Therefore, background noise signals such as autofluorescence from the substrate and leakage of the excitation light can be minimized, whereby the fluorescence sample can be detected with high sensitivity.

Further, in the fluorescence measurement apparatus according to the first embodiment, the top plate having, on its one surface, a reflection layer that reflects the excitation light irradiates the sample is further provided on the substrate, and the sample disposed on the substrate is surrounded with the wavelength selection means formed on the substrate and the reflection layer formed on the top plate. Therefore, the reflection light e2 that is the excitation light reflected by the wavelength selection means is again reflected by the dielectric multilayer of the top plate, and this reflection is repeated to realize multiple reflection in the sample. Therefore, the fluorescence emitted from the sample can be further amplified, and consequently, the fluorescence sample can be detected with higher sensitivity.

While in this first embodiment the dielectric multilayer has the multilayer structure in which two kinds of dielectric materials are alternately deposited, the present invention is not restricted thereto. The dielectric multilayer may have a multilayer construction in which three or more dielectric materials are combined.

APPLICABILITY IN INDUSTRY

Since a fluorescence measurement apparatus according to the present invention can detect a fluorescent signal with high sensitivity, it is applicable to single nucleotide polymorphism or bacteria test or virus test.

What is claimed is:

1. A fluorescence measurement apparatus, comprising:
    a substrate arranged to hold a sample that emits fluorescence when being irradiated with excitation light, said substrate having a well or a channel formed in an upper portion of said substrate;
    wavelength selection means for reflecting the excitation light and transmitting the fluorescence, said wavelength selection means being formed on an upper surface of said substrate and at a bottom surface of said well or said channel; and
    a light receiving unit for detecting fluorescence emitted by the sample which has passed through said wavelength selection means, said light receiving unit being disposed beneath said substrate,
    wherein the sample is disposed in the well or the channel in which said wavelength selection means is formed, and wherein the excitation light irradiates the sample from above said substrate.

2. A fluorescence measurement apparatus according to claim 1, wherein said wavelength selection means comprises a layer formed on the upper surface of the substrate.

3. A fluorescence measurement apparatus according to claim 2, wherein said layer comprises a dielectric multilayer.

4. A fluorescence measurement apparatus according to claim 3, wherein said dielectric multilayer comprises at least one dielectric material having a high refractive index and at least one dielectric material having a refractive index lower than that of the at least one dielectric material having the high refractive index alternately deposited on said substrate.

5. A fluorescence measurement apparatus according to claim 1, wherein said wavelength selection means comprises titanium dioxide layers and silicon dioxide layers which are alternately deposited.

6. A fluorescence measurement apparatus according to claim 1, further comprising:
    a filter for transmitting only the fluorescence that has been emitted from the sample and has passed through said wavelength selection means, said filter being disposed between said substrate and said light receiving unit.

7. A fluorescence measurement apparatus according to claim 1, wherein said substrate comprises a high-polymer material.

8. A fluorescence measurement apparatus according to claim 1, further comprising:
    a top plate having, on a surface of said top plate, a reflection layer for reflecting the excitation light, said top plate being arranged such that said reflection layer faces said substrate, and such that the excitation light is reflected multiple times in the sample by said wavelength selection means and said reflection layer.

9. A fluorescence measurement apparatus, comprising:
    a substrate arranged to hold a sample that emits fluorescence when being irradiated with excitation light, said substrate having a well or a channel formed in an upper portion of said substrate;
    wavelength selection means for reflecting the excitation light and transmitting the fluorescence, said wavelength selection means being formed on an upper surface of said substrate and at a bottom surface and inner side surfaces of said well or said channel; and
    a light receiving unit for detecting fluorescence emitted by the sample which has passed through said wavelength selection means, said light receiving unit being disposed beneath said substrate,
    wherein the sample is disposed in the well or the channel in which said wavelength selection means is formed, and wherein the excitation light irradiates the sample from above said substrate.

10. A fluorescence measurement apparatus according to claim 9, further comprising:
    a top plate having, on a surface of said top plate, a reflection layer for reflecting the excitation light, said top plate being arranged such that said reflection layer faces said substrate, and such that the excitation light is reflected multiple times in the sample by said wavelength selection means and said reflection layer.

11. A fluorescence measurement apparatus according to claim 9, wherein said wavelength selection means comprises a layer formed on the upper surface of the substrate.

12. A fluorescence measurement apparatus according to claim 11, wherein said layer comprises a dielectric multilayer.

13. A fluorescence measurement apparatus according to claim 12, wherein said dielectric multilayer comprises at least one dielectric material having a high refractive index and at least one dielectric material having a refractive index lower than that of the at least one dielectric material having the high refractive index alternately deposited on said substrate.

14. A fluorescence measurement apparatus according to claim 9, wherein said wavelength selection means comprises titanium dioxide layers and silicon dioxide layers which are alternately deposited.

15. A fluorescence measurement apparatus according to claim 9, further comprising:
a filter for transmitting only the fluorescence that has been emitted from the sample and has passed through said wavelength selection means, said filter being disposed between said substrate and said light receiving unit.

16. A fluorescence measurement apparatus according to claim 9, wherein said substrate comprises a high-polymer material.

* * * * *